(12) United States Patent
Neculaes et al.

(10) Patent No.: US 9,752,120 B2
(45) Date of Patent: Sep. 5, 2017

(54) ACTIVATED PLATELET COMPOSITION WITH TUNABLE GROWTH FACTOR LEVEL

(71) Applicant: General Electric Company, Schenectady, NY (US)

(72) Inventors: Vasile Bogdan Neculaes, Niskayuna, NY (US); Juan Jose Becerra, Altamont, NY (US); Christine Angela Morton, Troy, NY (US); Andrew Soliz Torres, Niskayuna, NY (US); Antonio Caiafa, Albany, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/674,971

(22) Filed: Mar. 31, 2015

(65) Prior Publication Data

US 2016/0289664 A1 Oct. 6, 2016

(51) Int. Cl.
*C12N 5/078* (2010.01)
*C12M 1/42* (2006.01)

(52) U.S. Cl.
CPC .......... *C12N 5/0644* (2013.01); *C12M 35/02* (2013.01); *C12N 2529/00* (2013.01)

(58) Field of Classification Search
CPC ... C12N 5/0644; C12N 2529/00; C12M 35/02
See application file for complete search history.

(56) References Cited

U.S. PATENT DOCUMENTS

| | | | |
|---|---|---|---|
| 6,326,177 B1 | 12/2001 | Schoenbach et al. | |
| 7,565,201 B2 | 7/2009 | Blackmore et al. | |
| 2014/0363412 A1 | 12/2014 | Neculaes et al. | |
| 2014/0363881 A1 | 12/2014 | Caiafa | |

FOREIGN PATENT DOCUMENTS

| | | |
|---|---|---|
| WO | 2015108619 A1 | 7/2015 |
| WO | 2015108778 A1 | 7/2015 |

OTHER PUBLICATIONS

Xiao et al. "Pulsed Power for Wound Healing" (2008) IEEE, IEEE International Power Modulators and High Voltage Conference, Proceedings of 2008, 69-72.*
U.S. Appl. No. 14/157,819, filed Jan. 17, 2014, Neculaes.
U.S. Appl. No. 14/158,106, filed Jan. 17, 2014, Caiafa.
Freitag, Julian et al.; "Photoactivated platelet-rich plasma therapy for a traumatic knee chondral lesion", BMJ Case Reports 2012: doi 10.1136/bcr-2012-006858 (abstract only).
AdiStem PhotoActivated PRP & Stem Cell Technology website downloaded 2014: http://www.adistem.com/technology/prp/.
Zhang, Jue, et al.; "Nanosecond pulse electric field (nanopulse): A novel non-ligand agonist for platelet activation", Archives of Biochemistry and Biophysics, Academic Press, US, Dec. 23, 2007 (Dec. 23, 2007), pp. 240-248, vol. No. 471, Issue No. 2, XP022503652, ISSN: 0003-9861.
Cai, Dong, et al.; "Interaction between carbon nanotubes and mammalian cells: characterization by flow cytometry and application", Nanotechnology, IOP, Bristol, GB, Aug. 27, 2008 (Aug. 27, 2008), p. 345102, vol. No. 19, Issue No. 34, XP020144491, ISSN: 0957-4484.
Neculaes, V. Bogdan, et al.; "Ex vivo platelet activation with extended duration pulse electric fields for autologous platelet gel applications", EWMA, Jan. 1, 2015 (Jan. 1, 2015), pp. 15-19, vol. No. 15, Issue No. 1, XP055278088.
International Search Report and Written Opinion issued in connection with corresponding PCT Application No. PCT/US2016/025990 dated Jun. 14, 2016.

* cited by examiner

*Primary Examiner* — Teresa E Knight
(74) *Attorney, Agent, or Firm* — Fletcher Yoder, P.C.

(57) ABSTRACT

Methods and systems for generating a tunable or customizable activated product composition are related. In certain embodiments, one or more of electric pulse parameters, flow rate, or sample container size are varied so as to generate the activated product composition. The activated product composition may be customized or optimized based for a particular patient or procedure.

12 Claims, 4 Drawing Sheets

ACTIVATED PLATELET COMPOSITION WITH TUNABLE GROWTH FACTOR LEVEL

BACKGROUND

The subject matter disclosed herein relates generally to platelet therapy used in various medical applications, such as treatments for surgery or trauma. Certain embodiments relate to platelet activation and providing levels of growth factor that can be specified or "tuned" by a user.

Use of platelet gel (also called "activated platelet rich plasma") is an emerging therapeutic approach that may be employed in clinic or other health care facility for a variety of applications, including promoting wound healing (such as after surgery) and hemostasis. In particular, interest in the use of platelet therapy as a wound healing treatment exists for many types of injuries and conditions, such as nerve injuries, tendinitis, osteoarthritis, cardiac muscle injury, and bone repair and regeneration. In addition, the derivation of the platelet gel used on a patient may be autologous, meaning that the platelets are derived from the patient's own tissues and/or fluids. Thus a blood sample, from the patient may be used to derive the platelet gel used to treat the patient.

By way of example, a doctor may draw blood from a patient. The blood may then be centrifuged to generate platelet rich plasma (PRP). Upon platelet activation, the platelets within the blood release growth factor and proteins that facilitate and promote the wound healing cascade. The clinical workflow may, therefore, involve drawing blood from the patient, centrifuging the blood to separate out the platelets, and performing an ex vivo platelet activation, such as using bovine thrombin. The activated platelets or platelet gel may then be applied to the wound or other treatment region. In instances where in vivo platelet activation is instead employed, the doctor may apply the PRP to the site without adding a platelet activator. Platelet activation, which includes growth factor release and clotting, is usually induced by the collagen within connective tissue.

For such ex vivo applications, where thrombin (e.g. bovine thrombin) is used to induce platelet activation, the resulting growth factor levels may be fixed based on the biologic response. That is the amounts and/or respective ratios or proportions of different growth factors are dictated by the nature of the thrombin-based activation. In such reactions, therefore, the clinician is unable to adjust or manipulate the respective amounts or proportions of different growth factors, and must instead make do with the conventional activation compositions.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a method for releasing growth is provided. In accordance with this method a sample is positioned with respect to electrodes of a pulse generating apparatus. A set of electric pulse parameters are specified. Different parameter values yield different levels of one or more growth in an activated product composition. The sample is exposed to one or more electric pulses generated in accordance with the parameter values. The sample, when exposed to the one or more electric pulses, yields the activated product composition having levels of the one or more growth factor determined at least in part by the set of electric pulse parameters.

In another embodiment, a method for releasing growth factors is provided. In accordance with this method a cuvette size is selected. Different cuvette sizes yield different levels of one or more factors in an activated product composition. A sample is placed within a cuvette of the selected size. The cuvette is placed within a sample holder of a pulse generating apparatus. The sample is exposed to one or more electric pulses. The sample, when exposed to the one or more electric pulses, yields the activated product composition having levels of the one or more growth factor determined at least in part by the cuvette size. The cuvette size can determine electric field (since the electric field is voltage divided by the cuvette spacing) and/or energy density.

In a further embodiment, a method for customizing an activated blood-derived cell treatment is provided. In accordance with this method a customized growth factor profile for treating a patient based on one or both of type of wound or a respective process of the wound healing cascade is determined. One or more electric pulse parameters and a cuvette size corresponding to the determined growth factor profile are selected. The growth factor profile may be tailored for the specific phase or process of the wound healing cascade. For example, the epithelization phase may require a growth factor profile that is reduced in TGFb1, a growth factor known to promote scarring. The granulation phase of a wound may require a growth factor profile rich in VEGF, a growth factor known to promote angiogenesis, formation of new blood vessels. A sample placed in a cuvette of the selected size is exposed to one or more electric pulses generated based on the selected electric pulse parameters to generate an activated product composition having the growth factor profile.

In an additional embodiment, an electric pulse-generating system is provided. In one embodiment, the system includes: a sample holder configured to accept at least two different sizes of cuvettes; pulse generating circuitry configured to generate one or more electrical pulses into a cuvette, when present in the sample holder; one or more user input devices configured receive user inputs; a non-transitory computer-readable memory storing one or more processor executable routines; and a processor configured to access and execute the one or more processor executable routines stored in the computer-readable memory. The processor executable routines, when executed cause acts to be performed comprising: receiving an input specifying one or more electric pulse parameters corresponding to a prescribed growth factor profile, wherein different electric pulse parameter values yield different levels of one or more growth factors in the growth factor profile; and generating one or more electric pulses based on the input using the pulse generating circuitry to generate an activated product composition having the prescribed growth factor profile.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
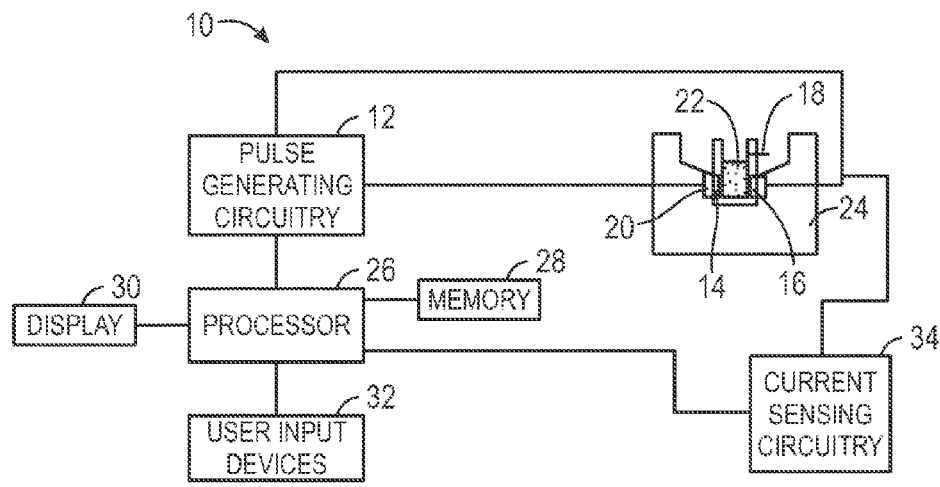
FIG. 1 is a schematic of a pulse generation system, in accordance with aspects of the present approach.

One or more specific embodiments of the present subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Platelet activation and/or aggregation may be used to treat wounds in vivo and/or ex vivo. For in vivo platelet activation, inactivated platelet rich plasma (PRP) is applied or injected at the site of injury and activated by naturally occurring compounds within the body, such as collagen present in the connective tissue.

During conventional ex vivo processes, platelets in drawn and separated blood are exposed to a platelet activating compound, such as thrombin, which induces the release of growth factors (e.g., platelet-derived growth factor (PDGF)). For example, for ex vivo platelet activation, a doctor may draw blood from a patient and centrifuge the blood sample to produce a platelet rich plasma (PRP) sample. Calcium chloride ($CaCl_2$) and a platelet activating compound, such as thrombin, may be added to the PRP sample to trigger platelet activation and to form a gel containing the growth factors that is then applied to the wound. However, this process does not allow any way to tailor or adjust the various levels of different growth factors relative to one another. Thus, the clinician must simply use the results of the activation process, regardless of whether the resulting growth factor mixture is optimized for the task at hand.

Present embodiments discussed herein relate to ex vivo platelet (or other cell) activation and growth factor release in response to exposure to one or more customizable energy exposure protocols, which allow for the release of different levels or amounts of growth factor in response to the activation parameters. In addition to the release of growth factors, the present approaches may also be used to control the release of other factors in an activation procedure. For example, activated platelets (or other cells in the exposed sample) may release endogenous antioxidants, reactive oxygen species, matrix metalloproteinase-2 (MMP-2) and other factors in a tunable or adjustable way in response to the approaches discussed herein. That is, tunable or customizable activation as discussed herein may involve not only customized release of growth factors, but of other factors (such as those listed above) that may be relevant to the wound healing process. Thus, it should be appreciated that, though specific examples or discussion herein may be provided in the context of growth factors, such examples and discussion also encompass other factors, such as those listed above, which may also be differentially released in response to different, customizable activation protocols.

The present approaches may be used with respect to various types of cells that release proteins, growth factors when activated, including (but not limited to) platelets, red blood cells, white blood cells, and so forth. In this manner, a platelet gel may be generated in which the levels of different growth factors in the platelet gel are tuned, such as to optimize the amount of certain factors produced, or adjusted relative to one another, such as to obtain a desired ratio or proportion of certain factors relative to others. This allows production of customized or optimized platelet gels that may have different growth factor profiles, different endogenous antioxidants profiles, different reactive oxygen species profiles, and so forth. This may be useful because different stages of the healing cascade (e.g., angiogenesis, epithelization, and so forth) may benefit from or be improved by different growth factors or other factors. Thus, by adjusting the growth factor levels based on a specific stage of the wound healing process, the wound healing process may be sped up.

Ex vivo platelet activation as discussed herein may involve exposing a blood sample, such as a PRP sample, or any suspension containing platelets, to electric pulses (e.g., exposure to pulsed electric fields) to trigger platelet activation, though exposure to other types of energy are also contemplated and encompassed. The methods for ex vivo growth factor release may or may not involve chemicals being added to the blood sample prior to electrical stimulation. As discussed herein, activation may or may not involve the destruction (e.g., lysis) of cells within the sample (e.g., red blood cells), depending on the parameters of the activation exposure. The process of cell lysis can be tuned depending on the parameters of the activation exposure. In certain embodiments electrical stimulation or activation may be applied using different electrical parameters (e.g. amplitude, voltage, electric field, energy density, current, pulse width, number of pulses, and so forth), with different parameters or combinations of parameters yielding different growth factor levels and/or different proportions of growth factors relative to one another. Correspondingly, exposures to other types of energy may include adjustment of one or more parameters typically associated with generation or exposure to that type of energy. Such differently formulated activated compositions may be used to achieve different biological or medical effects (e.g., enhanced wound healing), and the desired effect may therefore determine the electrical pulse parameters employed in activating a given cellular composition.

With the foregoing in mind, FIG. 1 shows schematically a pulse generation system 10 for ex vivo platelet (or other cellular product) activation and customizable or tunable growth factor release. The system 10 includes pulse generating circuitry 12 and opposing electrodes (or arrays of electrodes) 14 and 16. In the depicted embodiment, the electrodes 14 and 16 are spaced apart on opposing sides of a cuvette 18. That is, the cuvette 18 is disposed between the electrodes and the electrodes 14 and 16 are coupled to the pulse generating circuitry via contacts 20. That is, conductive coupling (i.e., contact coupling) is demonstrated in the depicted example. It should be understood, however, that this contact-coupling example is provided only to facilitate explanation and to provide a useful context for explaining the present approach, and is not the only suitable mechanism for exposing a sample (as discussed herein) to activation energy. For example, in other implementations, non-contact coupling techniques (such as capacitive or inductive coupling techniques) may be employed to accomplish the discussed energy coupling. Thus, as discussed herein, energy coupling to the platelet suspension should be understood as occurring via any suitable mechanism, whether involving contact between the sample container and conduit and electrodes (as shown in this example) or absent such contact using inductive or capacitive effects.

Regardless of the physical or structural implementation, the pulse generating circuitry 12, when in operation, electrically stimulates or activates a blood, blood component or platelet suspension sample 22 within the cuvette 18 so as to activate platelets or other cell types within the sample 22 that release proteins and/or growth factors when activated or stimulated. As discussed herein, this may take the form of applying pulsed electric fields to the sample contained within the cuvette 18 when the pulse generating circuitry 12 is operating, regardless of the manner in which the electrodes 14 and 16 and cuvette 18 are physically integrated or interfaced. In certain embodiments, the system 10 may be configured to accept or hold different sizes of cuvettes, such as cuvettes of different diameter or width.

In certain embodiments, the cuvette 18 may be disposable and/or removable from a sample holder 24 that incorporates the electrodes 14 and 16. Insertion of the cuvette 18 into the sample holder 24 and contact of the electrodes 14 and 16 with the contacts 20 allows the pulse generating circuitry 12 to produce electric pulses that span the sample 22. As will be appreciated, the cuvette 18 is merely one example of a suitable sample container, and other types of vessels configured to hold the sample 22, contact the electrodes 14 and 16, and conduct the electric pulses may be used in conjunction with the system 10. As discussed herein, the spacing between the electrodes 14 and 16 may influence the strength of the pulse's electric field, which is defined as the ratio of the applied voltage and the cuvette gap distance. For example, exposing a 1 cm wide cuvette to a 1 kV pulse yields a field strength of 1 kV/cm. Field strength, electrode separation distance, and other parameters related to the generated electrical pulses are factors, as discussed herein, that may be varied or adjusted to vary the growth factor levels with respect to one another during an activation procedure.

As may be appreciated, the depicted cuvette or container based activation system is suitable for a batch-type processing environment. However, a flow-through type processing environment may instead be employed, where a conduit instead passes through the electrodes 14 and 16, which may be on opposites sides of the conduit or surrounding the conduit. Such a flow through arrangement allows a sample to be continuously flowed through the conduit to be exposed to the pulsed electrical fields for activation, with the activated product being collected in a continuous or semi-continuous manner. In such an embodiment, in addition to, or instead of, the electrical parameters at the electrodes and/or the width between the electrodes 14 and 16, other parameters may also be adjusted so as to tune or customize the activated product. For example, the flow rate of the sample (e.g., a platelet suspension) through the conduit and/or the diameter of the conduit may also be accounted for or adjusted as a factor or parameter of the activation process. That is, in addition to the electrical parameters specified for the electrodes, one or both of the flow rate and the electrode spacing may determine the electrical field exposure (or field density exposure) experienced by the sample during activation.

In certain embodiments, the system may include control and input circuitry and may be implemented in a dedicated housing or may be coupled to a computer or other processor-based control system. For example, the system 10 may include or communicate with a processor 26 that controls the pulse generating circuitry 12. Additional components of the system 10 may include a memory 28 storing instructions that are executed by the processor 26. Such instructions may include protocols and/or parameters for generating the electric pulses using the pulse generating circuitry 12. The processor 26 may include, for example, general-purpose single- or multi-chip microprocessors. In addition, the processor 26 may be any conventional special purpose processor, such as an application-specific processor or circuitry. The memory 28 may be any suitable non-transitory computer-readable medium such as a random access memory, mass storage device, a solid state memory device, or removable memory. In addition, a display 30 may provide indications to an operator related to the operation of the system 10. The system 10 may include a user input device 32 (e.g., a keyboard, mouse, touchscreen, trackball, hand held device such as PDA or smart phone or any combination thereof) for activating the pulse generating circuitry 12, selecting or specifying appropriate pulse parameters, or selecting a pre-configured pulse profile from among a number of such profiles (such as profiles each corresponding to different stages of wound healing).

The pulse generation system 10 as discussed herein may be implemented as a single-purpose device for platelet or other cell-type activation or as a multi-purpose device that may be used for other electric field exposure applications, such as electroporation, accelerated cell growth via exposure to electrical stimulation in addition to platelet (or other cell-type) activation. Further, the system 10 may be configured to generate electric pulses according to one or more defined protocols and/or using one or more parameters that may be varied to generate different levels or proportions of growth factors, as discussed herein. The protocols may be generated by user input and/or may be stored in the memory 28 to be selected by the user, such as forma list or menu. In one embodiment, the pulse generating circuitry 12 may operate under control of the processor 26 to implement protocols that use a specified electric field strength, pulse length, total exposure time, flow rate (for a flow-through implementation) or other characteristic so as to generate a customized activated cellular composition (e.g., a gel customized to enhance a specific stage of wound healing) in which one or more growth factor levels are determined by the specified pulse parameter values. Such a protocol may be determined by empirical or theoretical studies, such as to correspond to a desired biological or medical effect (e.g., to a stage of wound healing) and/or to destruction or lysis of the cells of the sample during activation. In other embodiments, the system 10 may be configured to receive a user input related to one or more of the electric field strength, pulse length, flow rate, and/or total exposure time, i.e., the user can vary or specify one or more of these operational parameters. Further, the system 10 may be configured to generate a particular pulse shape or to generate a series of pulses that may differ from one another according to a user input and/or a stored protocol setting.

By way of example, in one embodiment, a pulse generated by the system 10 may have a duration from about 1 nanosecond to about 100 microseconds, and an electric field strength from about 0.1 kV/cm to about 350 kV/cm, depending on the application. As noted above, the electric field strength of the pulse is the applied voltage divided by the distance between the electrodes 14 and 16. While the pulses generated by the system 10 typically have an electric field strength of 0.1 kV/cm or greater, the pulses typically will not exceed the breakdown field of the suspension which includes the cells.

In some embodiments, the pulse generation system 10 may include sensing functionality. That is, the pulse generation system 10 may be configured to expose the sample 22 to a sensing signal, which may be an electric pulse with an electric field strength below that of the electric pulses used for cellular activation. The pulse generation system 10 may, as depicted in FIG. 1, include current sensing circuitry 34, which may acquire and/or process the sensing signal to estimate some of the electrical properties of the sample 22, including, but not limited to conductivity and permittivity. The current sensing circuitry 34 may be coupled to the processor 26, which may control the generation and processing of the sensing signal and, in some embodiments, may perform a portion of the processing. In other embodiments, the current sensing circuitry 34 may include a dedicated processor to control the processing of the sensing signal and may communicate with the processor 26 to report the results. Alternatively, the current sensing circuitry 34 may be integral with the pulse generating circuitry 12, providing inputs used in the generation of subsequent activation electrical pulses. In still other embodiments, the processing of the sensing signal may be performed by a dedicated processor as described above or the processor 26.

With respect to the various electric pulse factors or parameters, these factors include, but are not limited to: cuvette spacing (i.e., the width of the cuvette 18 across which the pulse is applied), flow rate (in a flow through embodiment), voltage, electric field (e.g., strength or density), current, pulse width, and the number of pulses applied. In one study, combinations of these parameters where tested in conjunction with other control or activation scenarios (e.g., the untreated platelet rich plasma (PRP), PRP+calcium chloride ($CaCl_2$), PRP+thrombin (e.g., bovine thrombin activated PRP). Table 1 summarizes the various combinations of electrical pulse parameters used in the study to activate platelets using electrical stimulation.

In addition, the last column of Table 1 indicates whether hemolysis occurred in the sample when exposed to pulses having the listed parameters. The electrical parameters can be adjusted so that hemolysis—red blood lysis—can be avoided or not. In the depicted example, hemolysis within the sample was observed in the two scenarios where electric field and current were highest. Thus, among other considerations, the desirability or undesirability of cell lysis or destruction within the sample may be a consideration in selecting electrical or other parameters (e.g., electrode spacing and flow rate) for an activation protocol.

TABLE 1

| Electrical Condition for Platelet Rich Plasma Stimulation | Cuvette Spacing (mm) | Voltage (kV) | Electric Field (kV/cm) | Current (A) | Pulse Width (µs) | # of Pulses | Hemolysis |
|---|---|---|---|---|---|---|---|
| 1 | 4 | 0.98 | 2.45 | 36 | 5 | 1 | No |
| 2 | 2 | 0.96 | 4.80 | 66 | 5 | 1 | No |
| 3 | 2 | 3.4 | 17 | 288 | 5 | 1 | Yes |
| 4 | 2 | 1.5 | 7.50 | 116 | 5 | 1 | Yes |
| 5 | 4 | 1.7 | 4.25 | 64 | 5 | 1 | No |

Figure 2:
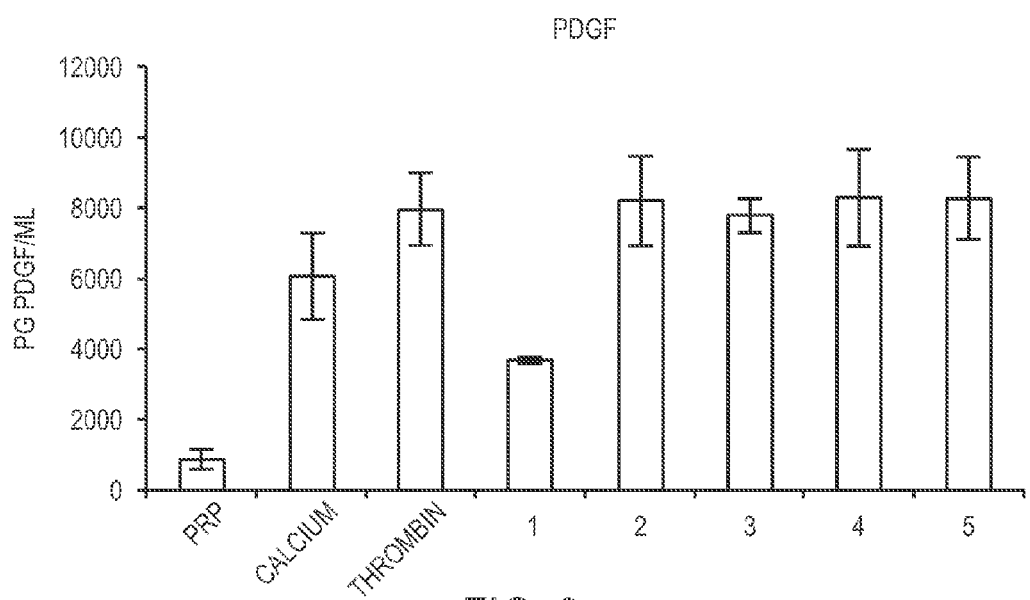
FIG. 2 is a graph depicting platelet derived growth factor (PDGF) levels in a platelet activated composition generated under a variety of scenarios, in accordance with aspects of the present approach.
Figure 3:
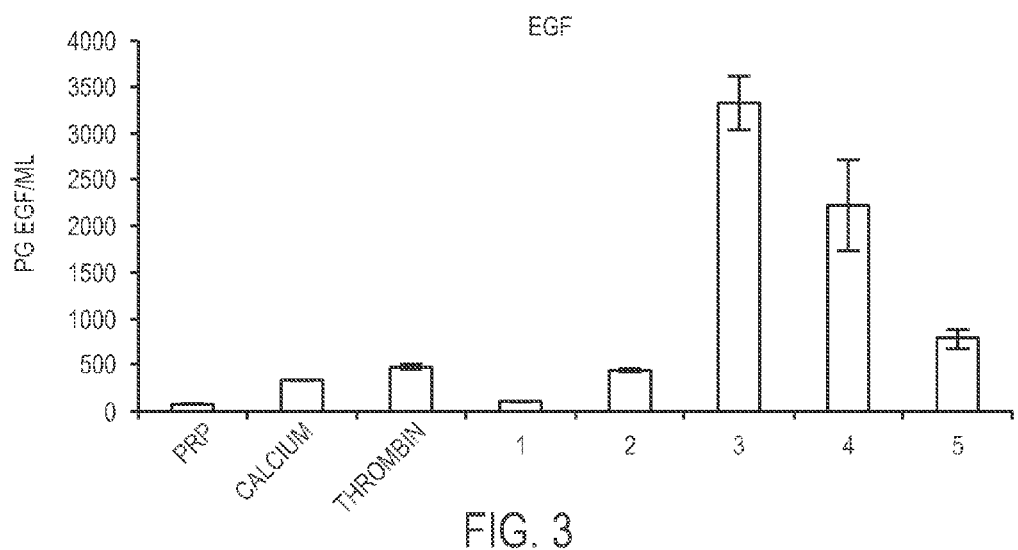
FIG. 3 is a graph depicting epidermal growth factor (EGF) levels in a platelet activated composition generated under a variety of scenarios, in accordance with aspects of the present approach.
Figure 4:
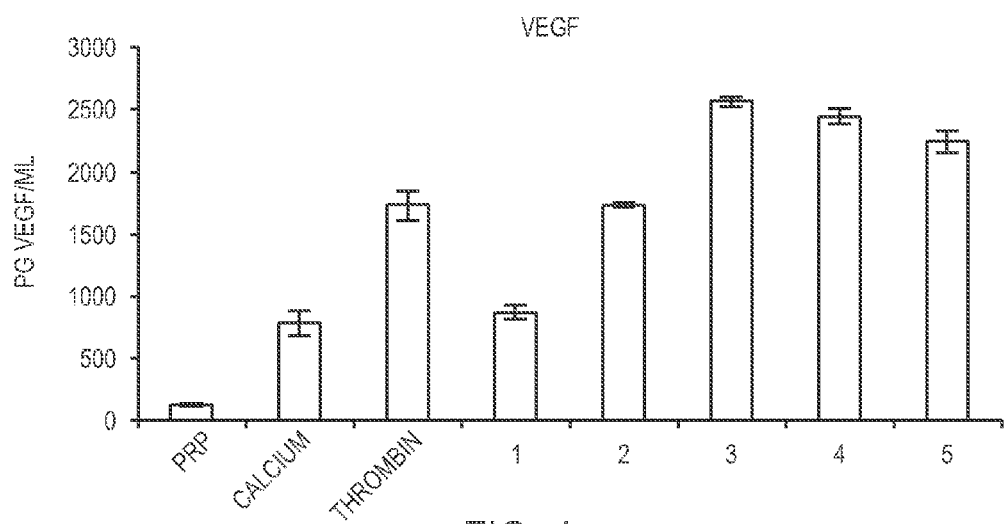
FIG. 4 is a graph depicting vascular endothelial growth factor (VEGF) levels in a platelet activated composition generated under a variety of scenarios, in accordance with aspects of the present approach.
Figure 5:
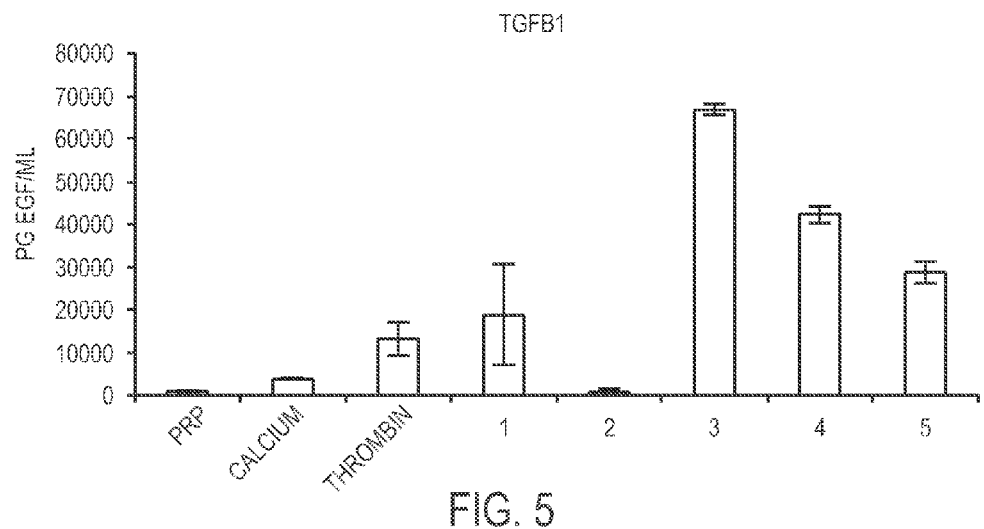
FIG. 5 is a graph depicting transforming growth factor beta 1 (TGFb1) levels in a platelet activated composition generated under a variety of scenarios, in accordance with aspects of the present approach.

Results of this study are shown in FIGS. 2-5, with FIG. 2 graphically depicting measured platelet derived growth factor (PDGF), FIG. 3 graphically depicting measured epidermal growth factor (EGF), FIG. 4 graphically depicting measured vascular endothelial growth factor (VEGF), and FIG. 5 graphically depicting measured transforming growth factor beta ($\beta$)1 (TGFb1). As shown in these results, differently parameterized electrical pulses yielded different levels of the respective growth factors not just between the electrical stimulation and non-electrical stimulation results, but also between differently parameterized electrical stimulation scenarios. In these figures, experimental conditions are: PRP=platelet rich plasma (not activated); Calcium=platelet rich plasma plus calcium chloride; Thrombin=platelet rich plasma, calcium chloride, and bovine thrombin (platelet activator); 1, 2, 3, 4, 5=platelet rich plasma, calcium chloride and activation via electrical stimulation conditions 1-5 shown in Table 1.

By way of example, with respect to PDGF and as shown in FIG. 2, the electrical pulses and cuvette spacing parameterized as shown in scenario 1 of Table 1, yielded levels of PDGF (~3,800 pg PDGF/mL) different than the other four scenarios (~8,000 pg PDGF/mL) and also different than the three non-electrical scenarios (~600 pg PDGF/mL for PRP, ~6,000 pg PDGF/mL for calcium, and ~8,000 pg PDGF/mL for thrombin). Thus, differing levels of PDGF within the activated platelet composition were obtained by manipulation of the electrical pulse properties, the cuvette spacing or width, and/or some combination of electrical and spatial factors, such as an energy density seen at the sample during the pulse.

Similarly, with respect to EGF and as shown in FIG. 3, the electrical pulses and cuvette spacing parameterized as shown in scenarios 1-5 of Table 1 yielded appreciably different levels of EGF for each numbered scenario, ranging from ~100 pg EGF/mL for scenario 1 to 3,300 pg EGF/mL for scenario 3. Further, the level of EGF measured for thrombin activated platelets was only ~500 pg EGF/mL, which was the highest level observed for the non-electrically activated samples. Thus, differing levels of EGF within the activated platelet composition were obtained by manipulation of the electrical pulse properties, the cuvette spacing or width, and/or some combination of electrical and spatial factors, such as an energy density seen at the sample during the pulse.

With respect to VEGF (FIG. 4), similar results are seen in that the different electrical pulse parameters and cuvette spacing as shown in scenarios 1-5 of Table 1, yielded different levels of VEGF for each numbered scenario, with scenarios 1 and 2 yielding ~800 pg VEGF/mL and ~1,750 pg VEGF/mL respectively, and scenarios 3-5 yielding between ~2,250 and ~2,500 pg VEGF/mL. Thus, as in the preceding examples, differing levels of VEGF within the activated platelet composition were obtained by manipulation of the electrical pulse properties, the cuvette spacing or width, and/or some combination of electrical and spatial factors, such as an energy density seen at the sample during the pulse.

Lastly, with respect to TGFb1, as shown in FIG. 5, the electrical pulses and cuvette spacing parameterized as shown in scenarios 1-5 of Table 1 yielded appreciably different levels of TGFb1 for each numbered scenario, ranging from less than 1,000 pg TGFb1/mL for scenario 2 to ~65,000 pg TGFb1/mL for scenario 3, with other scenarios falling between these values. Thus, as in the preceding examples, differing levels of TGFb1 within the activated platelet composition were obtained by manipulation of the electrical pulse properties, the cuvette spacing or width, and/or some combination of electrical and spatial factors, such as an energy density seen at the sample during the pulse. As a further example, electrical condition 2 produces lower levels of TGFb1 compared to thrombin activation (FIG. 5), but the same levels of PDGF-aa (FIG. 2), VEGF (FIG. 4), and EGF (FIG. 3) as thrombin. Since scientific literature suggests that TGFb1 is correlated to increased scarring, platelet gel created by electrical stimulation 2 described here may trigger lower scarring compared to platelet gel created via thrombin activation.

From the preceding examples, it can be seen that different growth factors are differentially released in response to varying different aspects of the electrical pulse and/or the electrode spacing. Therefore, as will be appreciated, based on the growth factor profile that is desired, an electrical pulse or sequence of pulses may be parameterized so as to release the desired levels of the desired growth factors. Further, pulse parameters may be varied or adjusted between pulses so as to target the release of a different growth factor by the different pulses.

It is also worth noting that spatial variations attributable to electrode spacing appears to sometimes be a factor in the differential growth factor release. For example, scenarios 2, 3, and 4 are all performed with 2 mm cuvette spacing, however, at least in the context of EGF, VEGF, and TGFb1 release, the different electrical pulse parameters each gave results where the amount of the respective growth factors released was greater for scenario 4 than for scenario 2, and greater for scenario 3 than scenario 4. That is, in these scenarios, the differentiating factor, due to cuvette spacing being held constant, is the differences in electrical pulse parameters.

Conversely, with respect to scenarios 2 and 5, roughly similar electrical pulse parameters in terms of electric field, current, pulse width, and number of pulses where applied but to cuvettes having different spacing (2 mm in scenario 2 and 4 mm in scenario 5). In this instance, different amounts of EGF, VEGF, and (particularly) TGFb1 were released in these two scenarios, strongly suggesting that cuvette spacing or some parameter derivative of cuvette spacing (such as energy density or electric field) is a differentiating factor. Hence, both electrical pulse parameters and spatial factors (separately or in a confounded manner) may differentially (e.g., preferentially) affect the release of one or more growth factors in an absolute sense and/or relative to other growth factors.

Using this knowledge, it is therefore possible to generate a platelet activation composition (e.g., a gel) having a desired amount of one or more specific growth (or other) factors, having a desired ratio or proportion of one or more factors relative to other factors, or having a particular profile of factors in an absolute or relative sense. That is, the platelet activation composition may be tuned or customized using a suitable combination of electrical pulse parameters, electrode spacing, and/or flow rate (in a flow-through implementation) allowing a clinician to generate or order a platelet activation composition having the desired medical or biological effects for a given patient, such as a composition specific to a stage of wound healing (example: higher VEGF for a wound that needs angiogenesis, new blood vessels, and so forth). In practice this may be implemented using preset options programmed into the system 10, such as selectable buttons or items of a menu or list of a graphical interface, where each option corresponds to a different medical effect or prescription and/or to a different set of pre-configured electrical pulse parameters and, thus, to a different growth factor profile of the composition. However, even in such an arrangement, options may be provided to a user to input custom or user-specified electrical pulse parameter.

Figure 6:
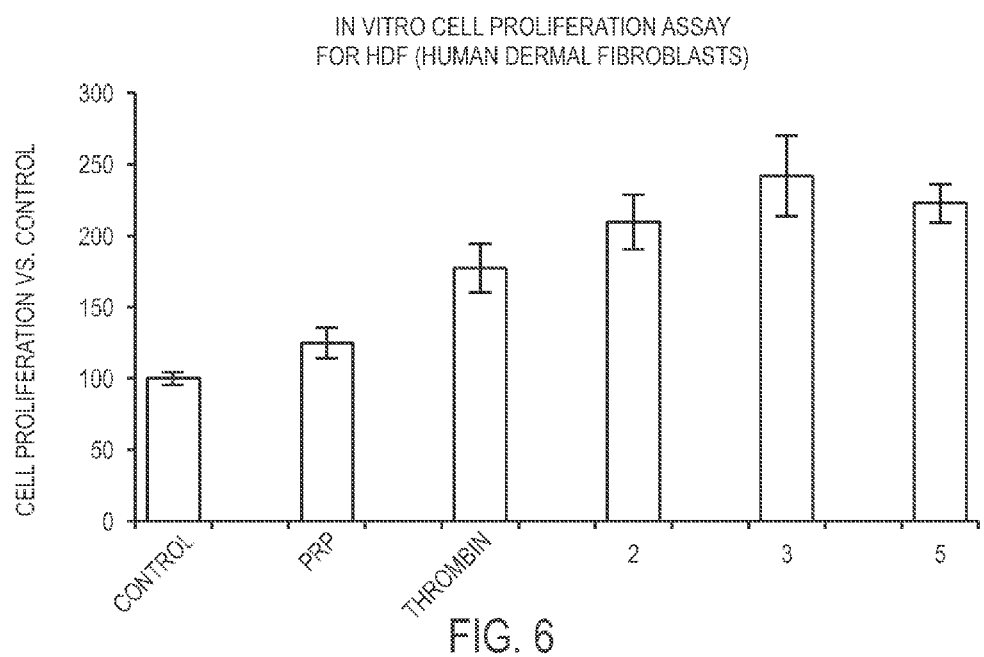
FIG. 6 depicts epithelization results of in vitro cell proliferation assays using growth factors obtained in accordance with certain of the present studies.
Figure 7:
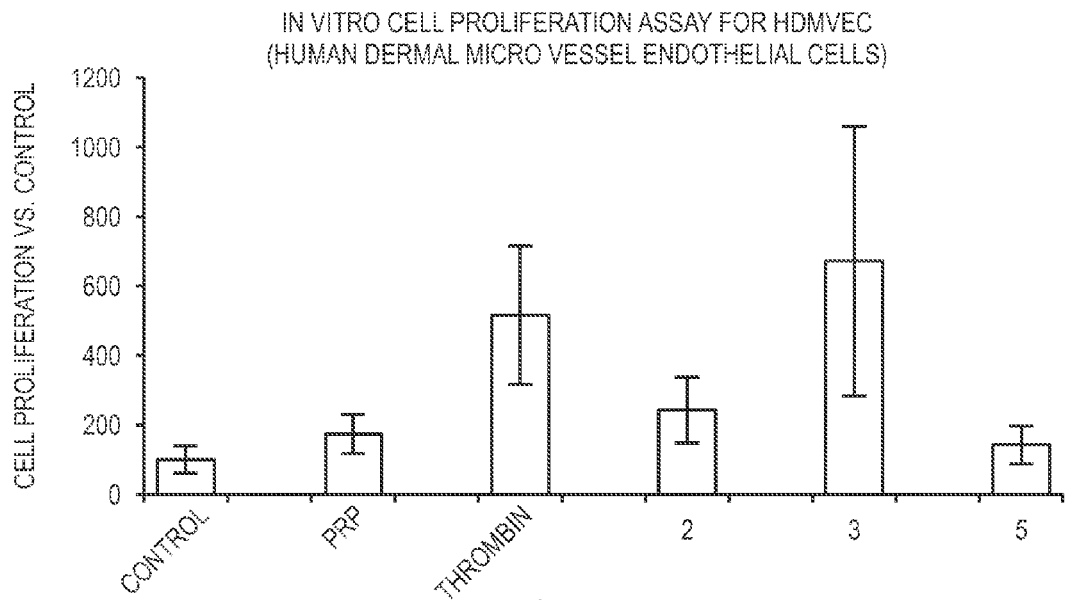
FIG. 7 depicts angiogenesis results of in vitro cell proliferation assays using growth factors obtained in accordance with certain of the present studies.

By way of further example, FIGS. 6 and 7 present results of in vitro cell proliferation assays using the growth factors from unactivated PRP, PRP activated with bovine thrombin, and electrical conditions 2, 3, and 5 from Table 1 (see the growth factor profiles in FIGS. 2, 3, 4 and 5). These assays used human dermal fibroblasts as a surrogate for epithelization (FIG. 6), and human dermal micro vessel endothelial cells as a surrogate for angiogenesis (FIG. 7). FIG. 6 shows that electrical conditions 2, 3, and 5 trigger cell proliferation at higher rates compared to thrombin activation (faster epithelization). But FIG. 7 shows that electrical condition 3 triggers higher proliferation rate compared to bovine thrombin activation (faster angiogenesis), while electrical conditions 2 and 5 show slower proliferation compared to bovine thrombin (slower angiogenesis). These assays demonstrate the potential for allowing a clinician to tune the wound healing effects using appropriate electrical stimulation of platelet rich plasma.

Figure 8:
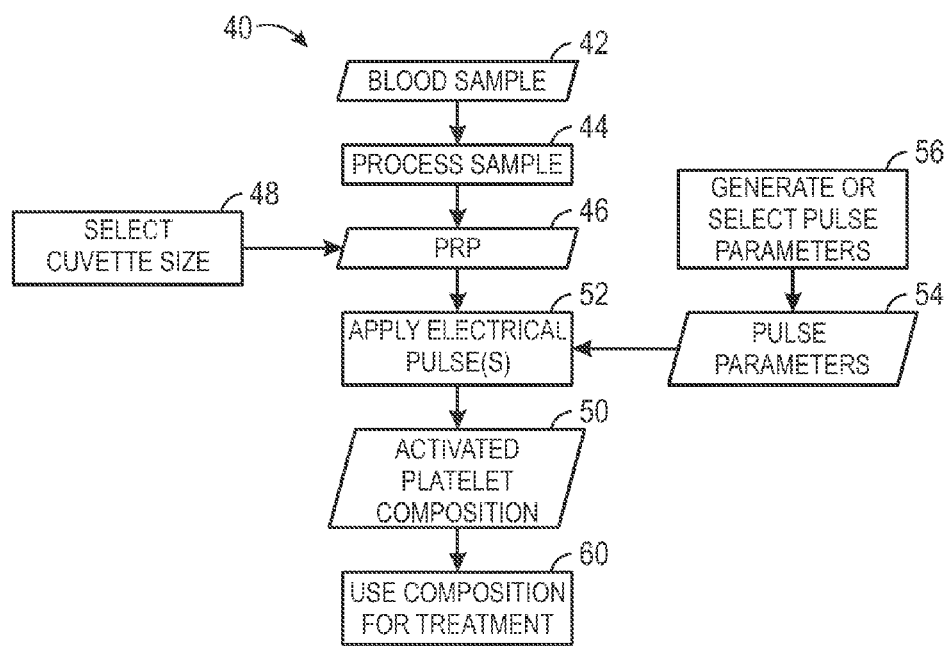
FIG. 8 is a process flow diagram depicting steps in the generation of a customizable or tunable platelet activated composition, in accordance with aspects of the present approach.

With the preceding in mind, FIG. 8 depicts an example of a process flow 40 that may be used to generate a platelet activated composition 50 as discussed herein. It should be understood that certain steps of the method 40 may be performed by an operator while other steps of the method may be performed by the system 10, such as executing one or more algorithms controlling configuration and/or application of the electrical pulses.

Turning to FIG. 8, a blood sample 42 (e.g., a whole blood sample) is, in one implementation initially processed (step 44) to generate a PRP sample 46. In an autologous implementation, the blood sample 42 may be obtained from the patient themselves, either during a prior visit or during current treatment session. In other implementations, the blood sample may be acquired from someone other than the patient. Further, the depicted processing step 44 may, in some instances, be absent, with the subsequent steps being understood to instead be performed on the blood sample 42. When performed, the processing step 44 may be based on one or more techniques suitable for platelet separation, such as centrifugation or filtration or any other suitable approach for generating a PRP sample 46 from a blood sample 42. In certain implementations, $CaCl_2$ may be added to the sample (whether PRP or whole blood), prior to exposure to one or more pulses at step 52 via the system 10.

In the depicted process flow, a step 48 is depicted in which an operator selects a cuvette or conduit size (e.g., an electrode spacing) in which the sample (whether PRP or whole blood) will be placed during exposure to electrical pulses. Any suitable electrode spacing may be employed (such as 2 mm, 4 mm, or other suitable sizes) and, as noted above, the selection of the cuvette size may be a factor in the levels of one or more growth factor present in the activated platelet composition, either in a relative sense (i.e., proportional to other growth factors) or an absolute sense (i.e., total amount or concentration present, independent of other growth factor levels).

The PRP or blood sample, within the selected cuvette size, is placed within the system 10 and is ready for exposure to one or more electrical pulses at step 52. Prior to pulse generation, the pulse parameters 54 may be selected or otherwise specified by the operator. Depending on the implementation, any electrical property of the pulse (including, but not limited to: voltage, electric field, current, and so forth) as well as the pulse width (i.e., duration) and number of pulses to be applied may be specified by the operator at step 56, either directly or by selection of a pre-established protocol (such as from a menu or list of protocols) corresponding to a prescribed activated platelet composition 50, such as a composition 50 optimized or customized for providing a specific biological or medical effect, when used (step 60).

Though platelet activation is referenced in certain of the present example, it should be appreciated that other cell types (e.g., red blood cells, white blood cells, and so forth) which may also be present in a platelet rich plasma can be activated so as to release proteins and/or growth factors as discussed herein. That is, the present approach may be generally understood to allow customizable release of proteins and/or growth factors form a variety of types of cells, not merely platelets, when such cells are activated. Further, as noted above, though growth factors have been called out by way of example in certain portions of the above discussion, other factors (e.g., endogenous antioxidants, reactive oxygen species, matrix metalloproteinase-2 (MMP-2)) may be present in the activated product and may have levels or proportions that are customized or tuned as discussed herein.

One or more of the disclosed embodiments, alone or in combination, may provide one or more technical effects useful for medical techniques for ex vivo platelet activation and release of growth and other factors. The present technique for ex vivo platelet activation allows for the use of cuvettes or conduits of different sizes and/or electrical pulses having different electrical properties, duration, and/or different numbers of such pulses to customize or tune the activated platelet composition with respect to the amount or concentration of one or more growth or other factors or the relative proportion of one or more factors with respect to other factors in the composition. In this manner, an activated platelet composition is generated having growth factor levels different than those observed when activation is accomplished by other means, including chemical means (e.g., by exposure to thrombin, collagen, calcium, and so forth). The technical effects and technical problems described in the specification are provided as examples only and are not intended to be limiting. It should be noted that the embodiments described in the specification may have other technical effects and can solve other technical problems.

While only certain features of the invention have been illustrated and described herein, many modifications and changes will occur to those skilled in the art. It is, therefore, to be understood that the appended claims are intended to cover all such modifications and changes as fall within the true spirit of the invention. Some of the embodiments can be used for in vivo platelet activation workflows. One could trigger growth factor release in PRP by electrical stimulation, without clotting, and inject this PRP at the site of the injury. The growth factors thus released can be used for wound healing at the site of the injury. Further, in certain embodiments, platelets can be also fully activated by the collagen within the connective tissue.

The invention claimed is:

1. A method for releasing growth factors, comprising:
   positioning a sample with respect to electrodes of a pulse generating apparatus;
   wherein the sample comprises one of a platelet rich plasma sample, a platelet suspension, or a whole blood sample;
   specifying a set of electric pulse parameters, wherein different parameter values yield different levels of at least one growth factor in an activated product composition;
   wherein the at least one growth factor comprise growth factors released by one or more of platelets, red blood cells, or white blood cells, including one or more of platelet derived growth factor, epidermal growth factor, vascular endothelial growth factor, or transforming growth factor beta 1 and wherein the level of at least one growth factor of the activated product composition is substantially equal to or larger than a level obtained using a thrombin activation; and
   exposing the sample to one or more electric pulses generated in accordance with the parameter values, wherein the sample, when exposed to the one or more electric pulses, yields the activated product composition having levels for the at least one growth factor adjustably controlled at least in part by the set of electric pulse parameters.

2. The method of claim 1, further comprising:
   selecting a container or conduit size from a plurality of container sizes; and
   placing the sample within the container having the selected size,
   wherein positioning the sample comprises placing the container holding the sample within a sample holder between the electrodes, wherein the activated product composition has levels of at least one growth factor determined at least in part by the container size.

3. The method of claim 1, wherein positioning the sample between the electrodes comprises flowing the sample through a conduit between the electrodes, wherein the activated product composition has levels of the at least one growth factor determined at least in part by one or both of the conduit diameter or the flow rate of the sample through the conduit.

4. The method of claim 1, wherein the set of electric pulse parameters comprise one or more of a voltage, an electric field, a current, a pulse width, an energy density, energy per platelet, or a number of pulses.

5. The method of claim 1, wherein the sample comprise cells that are not lysed in response to the one or more electric pulses.

6. A method for releasing growth factors, comprising:
   selecting a cuvette size from among a plurality of cuvette sizes, wherein different cuvette sizes of the plurality yield different levels of one or more growth factors in an activated product composition;
   placing a sample within a cuvette of the selected size;
   wherein the sample comprises one of a platelet rich plasma sample, a platelet suspension, or a whole blood sample;
   placing the cuvette within a sample holder of a pulse generating apparatus;
   exposing the sample to one or more electric pulses, wherein the sample, when exposed to the one or more electric pulses, yields the activated product composition having levels of the one or more growth factors adjustably controlled at least in part by the cuvette size;
   wherein the one or more growth factors comprise growth factors released by one or more of platelets, red blood cells, or white blood cells, including one or more of platelet derived growth factor, epidermal growth factor, vascular endothelial growth factor, or transforming growth factor beta 1; and
   wherein the level of the at least one growth factor of the activated product composition is substantially equal to or larger than a level obtained using a thrombin activation.

7. The method of claim 6, further comprising:
   specifying a set of electric pulse parameters, wherein different parameter values yield different levels of one or more growth factors in the activated product composition, and wherein the activated product composition has levels of the one or more growth factor determined at least in part by the set of electric pulse parameters.

8. The method of claim 7, wherein the set of electric pulse parameters comprise one or more of a voltage, an electric field, a current, a pulse width, an energy density, or a number of pulses.

9. The method of claim 6, wherein the sample comprises cells that are not lysed in response to the one or more electric pulses.

10. A method for customizing an activated blood-derived cell treatment, comprising:
    adjustably controlling a customized growth factor profile for treating a patient based on one or both of type of wound or a respective process of the wound healing cascade;
    wherein adjustably controlling the customized growth factor profile comprises adjustably controlling an amount of one or more growth factors to be present in the activated product composition relative to an amount of one or more different growth factors to be present in the activated product composition;
    wherein the growth factors consist of platelet derived growth factor, epidermal growth factor, vascular endothelial growth factor and transforming growth factor beta 1;
    selecting one or more electric pulse parameters and a cuvette size corresponding to the adjustably controlled growth factor profile;
    exposing a sample placed in a cuvette of the selected size to one or more electric pulses generated based on the selected electric pulse parameters;
    wherein the sample comprises one of a platelet rich plasma sample, a platelet suspension, or a whole blood sample; and
    generating an activated product composition having the customized growth factor profile.

11. The method of claim 10, wherein selecting the one or more electric pulse parameters comprises specifying values for one or more of a voltage, an electric field, a current, a pulse width, an energy density, or a number of pulses.

12. The method of claim 10, wherein selecting the one or more electric pulse parameters comprises selecting a preconfigured pulse profile from a plurality of preconfigured pulse profiles.

* * * * *